(12) United States Patent
Harvey et al.

(10) Patent No.: US 12,403,195 B2
(45) Date of Patent: *Sep. 2, 2025

(54) SENSITIZING CELLS TO PROTON RADIATION

(71) Applicants: Humanetics Corporation, Minneapolis, MN (US); The Trustees of the University of Pennsylvania, Philadelphia, PA (US)

(72) Inventors: Adam J. Harvey, Minneapolis, MN (US); Michael D. Kaytor, Maplewood, MN (US); Keith Cengel, Bala Cynwyd, PA (US); Eric Stanton Diffenderfer, Wayne, PA (US)

(73) Assignees: Humanetics Corporation, Excelsior, MN (US); Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,816

(22) Filed: Aug. 31, 2023

(65) Prior Publication Data

US 2024/0173412 A1 May 30, 2024

Related U.S. Application Data

(63) Continuation of application No. 17/486,499, filed on Sep. 27, 2021, now Pat. No. 11,779,644, which is a
(Continued)

(51) Int. Cl.
*A61K 41/00* (2020.01)
*A61K 9/00* (2006.01)
(Continued)

(52) U.S. Cl.
CPC ........ *A61K 41/0038* (2013.01); *A61K 9/0019* (2013.01); *A61K 9/0053* (2013.01);
(Continued)

(58) Field of Classification Search
CPC .............. A61K 41/0038; A61K 9/0019; A61K 9/0053; A61K 9/10; A61K 9/51;
(Continued)

(56) References Cited

U.S. PATENT DOCUMENTS 3,465,153 A    9/1969   Libby
6,094,760 A    8/2000   Nonka et al.
(Continued)

FOREIGN PATENT DOCUMENTS

EP      2832356      2/2015

OTHER PUBLICATIONS

Bei Zhang, Jia-yin Liu, Jin-shun Pan, Su-ping Han, Xiao-xing Yin, Bing Wang, Gang Hu, Combined Treatment of Ionizing Radiation With Genistein on Cervical Cancer Hela Cells, Journal of Pharmacological Sciences, vol. 102, Issue 1,2006, pp. 129-135, ISSN 1347-8613, https://doi.org/10.1254/jphs. FP0060165 (Year: 2016).*
(Continued)

*Primary Examiner* — Sunita Reddy
(74) *Attorney, Agent, or Firm* — Fish & Richardson P.C.

(57) ABSTRACT

Materials and methods for enhancing the effectiveness of proton radiation therapy (e.g., high linear energy transfer (LET) proton radiation therapy) against tumor cells are provided herein.

18 Claims, 7 Drawing Sheets

Related U.S. Application Data continuation of application No. 16/145,787, filed on Sep. 28, 2018, now Pat. No. 11,129,894.

(60) Provisional application No. 62/565,970, filed on Sep. 29, 2017.

(51) Int. Cl.

| *A61K 9/10* | (2006.01) |
|---|---|
| *A61K 9/51* | (2006.01) |
| *A61K 31/353* | (2006.01) |
| *A61K 47/32* | (2006.01) |
| *A61N 5/10* | (2006.01) |
| *A61P 35/00* | (2006.01) |

(52) U.S. Cl.
CPC ............... *A61K 9/10* (2013.01); *A61K 9/51* (2013.01); *A61K 31/353* (2013.01); *A61K 47/32* (2013.01); *A61N 5/10* (2013.01); *A61P 35/00* (2018.01); *A61N 2005/1087* (2013.01); *A61N 2005/1098* (2013.01)

(58) Field of Classification Search
CPC ........ A61K 31/353; A61K 47/32; A61K 5/10; A61K 35/00; A61K 2005/1087; A61K 2005/1098
USPC ............................................. 600/1–8
See application file for complete search history.

(56) References Cited

U.S. PATENT DOCUMENTS

| 8,551,530 | B2 | 10/2013 | Elder, Jr. et al. |
|---|---|---|---|
| 9,084,726 | B2 | 7/2015 | Egberg et al. |
| 11,129,894 | B2 | 9/2021 | Harvey et al. |
| 11,419,827 | B2 | 8/2022 | Harvey et al. |
| 11,779,644 | B2 | 10/2023 | Harvey et al. |
| 2005/0070508 | A1 | 3/2005 | Lou et al. |
| 2005/0090509 | A1* | 4/2005 | Lou ..................... A61P 35/00 544/278 |
| 2007/0293458 | A1 | 12/2007 | Shamsuddin et al. |
| 2009/0263331 | A1 | 10/2009 | Wu et al. |
| 2012/0164190 | A1* | 6/2012 | Elder ....................... A61K 9/10 977/773 |
| 2013/0053362 | A1 | 2/2013 | Castro et al. |
| 2013/0137916 | A1* | 5/2013 | Goer ................... A61K 31/4168 604/20 |
| 2014/0045950 | A1 | 2/2014 | Lacko et al. |
| 2014/0050723 | A1* | 2/2014 | Hansen ................ A61K 31/513 435/375 |
| 2014/0341802 | A1 | 11/2014 | North et al. |
| 2015/0126597 | A1* | 5/2015 | Kaytor ..................... A61P 35/00 514/456 |
| 2016/0078167 | A1 | 3/2016 | Rosner et al. |
| 2019/0099491 | A1 | 4/2019 | Harvey et al. |
| 2019/0380972 | A1 | 12/2019 | Harvey et al. |
| 2020/0001111 | A1* | 1/2020 | Isrow ..................... A61K 33/00 |
| 2022/0152201 | A1 | 5/2022 | Harvey et al. |
| 2022/0401375 | A1 | 12/2022 | Harvey et al. |

OTHER PUBLICATIONS

Mayer R, Lin L, Fager M, Douglas D, McDonough J, Carabe A. Proposed linear energy transfer areal detector for protons using radiochromic film. Rev Sci Instrum. Apr. 2015;86(4):044301. doi: 10.1063/1.4917418. PMID: 25933872. (Year: 2015).*

Sridharan et al., "Understanding cancer development processes after HZE-particle exposure: roles of ROS, DNA damage repair and inflammation" Radiation Res 183:1-26, 2015.

Verdrengh et al., "Genistein as an anti-inflammatory agent" Inflammation Res. 52(8):341-346, 2003.

Wu et al., "Risk of acute radiation syndromes due to solar particle events" In: McPhee and Charles (Eds.), Human Health and Performance Risks of Space Exploration Missions, NASA, pp. 171-190, 2009.

Zhang et al., "Combined treatment of ionizing radiation with genistein on cervical cancer HeLa cells" Journal of pharmacological sciences, 102(1):129-135, Jan. 1, 2006.

Zhang et al., "Genistein induces G2/M cell cycle arrest and apoptosis via ATM/p53- dependent pathway in human colon cancer cells" Int. J Oncol. 43(1):289-296, 2013.

Myclevelandclinic.org [online], "Chronic Obstructive Pulmonary Disease (COPD)," Aug. 19, 2024, retrieved on Apr. 21, 2024 from URL <https://my.clevelandclinic.org/health/diseases/8709-chronic-obstructive-pulmonary-disease-copd, 9 pages.

* cited by examiner

SENSITIZING CELLS TO PROTON RADIATION

CROSS-REFERENCE TO RELATED APPLICATIONS

This application is a continuation of U.S. application Ser. No. 17/486,499, filed on Sep. 27, 2021, now U.S. Pat. No. 11,779,644, which is a continuation of U.S. application Ser. No. 16/145,787, filed on Sep. 28, 2018, now U.S. Pat. No. 11,129,894, which claims benefit of priority from U.S. Provisional Application Ser. No. 62/565,970, filed on Sep. 29, 2017.

TECHNICAL FIELD

This document relates to materials and methods for enhancing the effectiveness of radiation therapy against tumor cells, and more particularly to materials and methods for enhancing the effectiveness of high linear energy transfer (LET) proton radiation therapy against tumor cells.

BACKGROUND

Radiation therapy is an effective treatment modality to control many cancers. Mainstream radiotherapy devices use X-rays as the form of ionizing radiation to damage malignant tumors. Unfortunately, X-ray radiation can have detrimental effects on normal tissue, since the energy of the photons that make up X-ray beams is deposited in both normal and tumor tissue along the path of the beam. Proton radiation therapy, on the other hand, can be controlled such that the protons release their cancer-fighting energy at a selected position within the body. This is achieved by controlling the energy characteristics of the proton beam, since the probability that a proton is absorbed by matter as it travels through a medium is dependent on its energy and the distance it travels. The point at which the highest energy release occurs is called the "Bragg peak." Clinicians can modulate the Bragg peak's size and distance to cause the most damage to targeted tumor cells. In addition, proton beams can be conformed to the shape and depth of a patient's tumor, thus minimizing absorption in healthy tissues and organs.

SUMMARY

This document is based, at least in part, on the discovery that compositions containing genistein can be useful for sensitizing tumor tissue to radiation therapy, and particularly to radiotherapy with high LET proton radiation. Genistein acts as a selective agonist of estrogen receptor beta and has significant cell-signaling activities that affect how cells respond to radiation damage, beyond simply affecting the incidence of damage itself. As described herein, compositions (e.g., suspension formulations) that contain genistein (e.g., genistein nanoparticles) as the active ingredient can be used as sensitizing agents that enhance the effectiveness of radiation (e.g., high LET proton radiation) against tumors.

In a first aspect, this document features a method for sensitizing tumor cells to high LET proton radiation. The method can include contacting the tumor cells with a composition containing one or more pharmaceutically acceptable carriers and nanoparticulate genistein at a concentration between about 250 mg/mL and about 500 mg/mL, and subsequently contacting the tumor cells with the high LET proton radiation. The tumor cells can be lung cancer cells, prostate cancer cells, head and neck cancer cells, pancreatic cancer cells, colon/colorectal cancer cells, bladder cancer cells, thyroid cancer cells, breast cancer cells, liver cancer cells, ovarian cancer cells, endometrial cancer cells, cervical cancer cells, kidney cancer cells, brain cancer cells, or melanoma cells. In some cases, the tumor cells can be non-small cell lung cancer (NSCLC) cells. The method can include contacting the tumor cells with the genistein composition about 24 hours prior to contacting the tumor cells with the high LET proton radiation.

In another aspect, this document features a method for treating a mammal identified as having a solid tumor and slated to undergo treatment with high LET proton radiotherapy. The method can include administering to the mammal a composition containing one or more pharmaceutically acceptable carriers and nanoparticulate genistein at a concentration between about 250 mg/mL and about 500 mg/mL. The method can include administering the composition to the mammal at about 24 hours before the onset of the high LET proton radiotherapy. The method can include administering the composition to the mammal throughout the course of the high LET proton radiotherapy. The method can include administering the composition to the mammal after completion of the high LET proton radiotherapy. The method can include administering the composition to the mammal at least once a day during the course of the high LET proton radiotherapy treatment. The method can include administering the composition to the mammal at least twice a day during the course of the high LET proton radiotherapy treatment. The tumor can be a lung tumor, a prostate tumor, a head and neck tumor, a pancreatic tumor, a colon/colorectal tumor, a bladder tumor, a thyroid tumor, a breast tumor, a liver tumor, an ovarian tumor, an endometrial tumor, a cervical tumor, a kidney tumor, a brain tumor, or a melanoma. In some cases, the tumor can be a non-small cell lung cancer (NSCLC) tumor. The mammal can be a human. The method can include administering the composition to the mammal at a dose of about 250 mg/day to 500 mg/day, about 500 mg/day to 1,000 mg/day, about 1,000 mg/day to about 5,000 mg/day, or about 5,000 mg/day to about 10,000 mg/day. The tumor can contain cells having a KRAS or p53 signature. The tumor can contain cells that express ERβ. The can further include contacting the tumor in the mammal with high LET proton radiation. Due to the administration of the composition, the tumor can be effectively treated with a dose of radiotherapy that is at least 10% less than the dose of radiotherapy that would be administered to a corresponding tumor in a mammal not treated with the composition. Due to the administration of the composition, the tumor can be more effectively treated with the high LET proton radiotherapy, as compared to the effectiveness of the same dose of high LET proton radiotherapy administered to a corresponding tumor in a mammal not treated with the composition. The nanoparticulate genistein composition can have a particle size distribution characterized by a d(0.5) less than or equal to 0.3 μm. The one or more pharmaceutically acceptable carriers can form a suspension medium, and can include a water soluble polymer comprising a polyvinylpyrrolidone. The one or more pharmaceutically acceptable carriers can include a nonionic surfactant, a diluent, or a buffer. The nonionic surfactant can be present in an amount ranging from about 0.01% to about 10% by weight (w/w). The amount of water soluble polymer can be about 0.5% to about 15% (w/w). The composition can contain a diluent and a preservative. The composition can further contain a nonionic surfactant. The nanoparticulate genistein can be present in the composition at an amount ranging up to about 50%

(w/w) (e.g., an amount of about 20% to about 35% (w/w). The method composition can have a nanoparticulate genistein concentration of about 325 mg/mL. The composition can have a pH of about 2 to about 12. The composition can be formulated as a tablet, a capsule, or a gelatin capsule. The method can include administering the composition orally (e.g., as an oral suspension), intramuscularly, subcutaneously, or intravenously.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
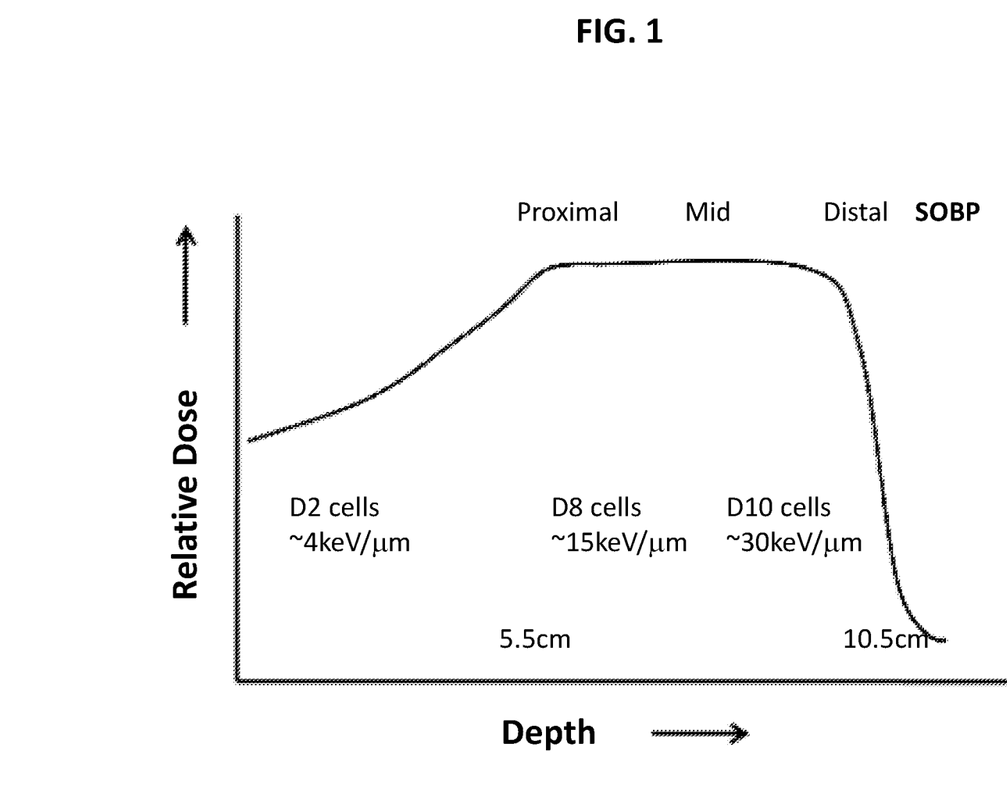
FIG. 1 is a graph plotting a representative Bragg peak.

Proton radiation differs from photonic gamma/X-ray radiation from a physical perspective. Protons deposit their energy at a specific depth as they pass through various media, according to the energy of the proton. This aspect of proton radiation can be exploited in radiotherapy, by modulating the energy of the beam to target a depth of tissue where the maximal energy will be deposited. Thus, as proton radiation enters the body, less of its energy is deposited per unit path length (low unrestricted linear energy transfer or low LET protons) as it travels to the target area. At the end of its path (the Bragg peak), the amount of energy deposited per unit path length (unrestricted LET) is much higher (high LET protons). A graph showing a representative Bragg peak is shown in FIG. 1. To facilitate treating larger areas with protons, the energy of the proton beam can be modulated to create a spread out Bragg peak (SOBP), such that the LET is lowest at the entrance and highest at the end of the SOBP.

In the experiments described herein, a R10.5M5 double scattered proton beam (a proton beam with a maximum range of 10.5 cm where the SOBP comprises the final 5 cm) was utilized with precise positioning of culture dishes at specific points at the entrance, middle, and end of the SOBP. For this beam, the "low LET" was at 2 cm depth, corresponding to about 4 keV/μM, and the high LET was at 10 cm depth, corresponding to about 30 keV/μM. As used herein, the term "low LET" refers to about one to about ten (e.g., about one to three, two to four, three to five, four to six, five to seven, six to eight, seven to nine, or eight to ten) keV/μM unrestricted LET as determined from tables of proton stopping power in liquid water, available from the National Institute of Standards and Technology (stopping power and range tables for protons; "PSTAR"). The term "high-LET" refers to about 20 to 40 (e.g., 20 to 25, 25 to 30, 30 to 35, or 35 to 40) keV/μM, again as determined from PSTAR unrestricted LET tables.

The results discussed in the Examples below are consistent with LET-dependent radiosensitization by nanoparticulate genistein, where the higher the LET that is delivered, the more the genistein is capable of radiosensitizing the tumor cells. These effects also may be related to the genetics of the tumor type.

As described herein, compositions containing genistein can be used as agents to increase the effectiveness of radiation (e.g., proton radiation, including high LET proton radiation) against tumor cells, either in vitro or in vivo. The methods provided herein therefore include using genistein-containing compositions to sensitize tumor cells to proton radiation therapy, and may result in prolonged survival (e.g., progression-free or overall survival) of cancer patients treated as described herein.

Genistein (5,7-dihydroxy-3-(4-hydroxyphenyl)-chromen-4-one (IUPAC), 5,7-dihydroxy-3-(4-hydroxyphenyl)-4H-1-benzopyran-4-one, 5,7,4'-trihydroxyisoflavone, 4',5,7-trihydroxyisoflavone) is a phytoestrogen in the category of isoflavones. Its chemical structure is shown in Formula (1):

Formula (1)

Genistein is one of several known isoflavones that are normally found in plants. The main sources of natural genistein are soybeans and other legumes. Genistein also is commercially available, and may be obtained in synthetic, purified form (e.g., from DSM Nutritional Products, Inc., Parsippany, NJ).

Genistein has antioxidant and anti-inflammatory properties (Verdrengh et al., *Inflammation Res.* 52(8):341-346, 2003; Polkowski and Mazurek, *Acta Poloniae Pharmaceutica-Drug Research* 57(2):135-155, 2000; and Kruk et al., *Luminescence: J. Biol. Chem. Luminescence* 20(2):81-89, 2005). Genistein also has effects on cell cycle division (Zhang, et al., *Int. J. Oncol.* 43(1):289-296, 2013) that likely are mediated by its selective activation of estrogen receptor beta (ERB) (Kuiper et al., *Endocrinol* 139(10):4252-4263, 1998). In addition, genistein can inhibit protein tyrosine kinase activity, modulating signal transduction pathways involved in cell death and survival. The antioxidant properties of genistein may relate to genistein's ability to scavenge ROS, which are directly implicated in the formation of DNA double strand breaks. Thus, genistein may have beneficial effects in individuals exposed to radiation, acting to protect healthy tissue and mitigate the effects of radiation in individuals accidently or intentionally exposed to radiation. As described herein, however, genistein also can act to sensitize tumor tissue to radiation, including high LET proton radiation.

As described elsewhere (see, e.g., U.S. Pat. No. 8,551,530), genistein nanoparticles can have improved oral and/or parenteral bioavailability as compared to genistein that is not in nanoparticle form. Nanoparticle formulations can contain sub-micron size genistein particles, which can be manufactured using a wet nanomilling process that reduces genistein to a median particle size of less than 0.2 μm. See, e.g., U.S. Pat. No. 8,551,530. In addition, pharmacokinetic experiments using such a genistein nanosuspension in mice, canines, and humans have demonstrated increased oral bioavailability as compared to formulations containing non-micronized genistein. See, e.g., FIGS. 4-7 of U.S. Pat. No. 8,551,530.

In some embodiments, the genistein compositions used in the methods provided herein can be formulations that include genistein in a solution containing one or more pharmaceutically acceptable carriers, excipients, and/or diluents. In some embodiments, the genistein compositions used in the methods provided herein can be suspension formulations that include nanoparticulate genistein suspended in a medium containing one or more pharmaceutically acceptable carriers, excipients, and/or diluents. Pharmaceutically acceptable carriers, excipients, and diluents suitable for therapeutic use include those described, for example, in *Remington's Pharmaceutical Sciences*, Maack Publishing Co. (A. R. Gennaro (ed.), 1985). In some cases, polyethylene glycol (PEG) can be used as a carrier in a composition that also contains genistein that is not in nanoparticle form.

A genistein composition also can contain one or more other components, as described herein (e.g., one or more pharmaceutically acceptable excipients that form a suspension medium, such as a water soluble polymer, a nonionic surfactant, a diluent, or a buffer). In some embodiments, a genistein composition can include a suspension of genistein (e.g., nanoparticulate genistein) in a non-aqueous medium, such as an edible lipid, oil, or fat from a plant or animal source (e.g., olive oil, sunflower oil, corn oil, soy oil, marine oil, coconut oil, palm oil, palm kernel oil, cotton seed oil, safflower oil, sesame oil, peanut oil, almond oil, cashew oil, pecan oil, pine nut oil, macadamia oil, orange oil, flax seed oil, lemon oil, walnut oil, borage oils, fish oils, and dairy derived fats). See, e.g., U.S. Pat. No. 9,084,726. In some cases, a genistein composition can include a suspension (e.g., a suspension of nanoparticulate genistein) in a medium including one or more water soluble polymers and one or more nonionic surfactants. See, e.g., U.S. Pat. No. 8,551,530. Nonionic surfactants can facilitate wetting and aid in preventing agglomeration of nanoparticulate genistein, for example. Suitable nonionic surfactants include, without limitation, polysorbates, poloxamers, polyoxyethylene castor oil derivatives, bile salts, lecithin, 12-hydroxystearic acid-polyethylene glycol copolymer, and the like. In some embodiments, a genistein composition can include a nonionic surfactant selected from the group consisting of polysorbate 80 (TWEEN® 80), polysorbate 20 (TWEEN® 20), Poloxamer 188, and combinations thereof. The total nonionic surfactant content in the genistein compositions utilized in the methods provided herein can range from about 0.01% to about 10% by weight (w/w) (e.g., about 0.2% to about 5% (w/w), about 0.2% to about 2% (w/w), about 0.2% to about 1% (w/w), about 0.2% to about 0.6% (w/w), and about 0.2% to about 0.8% (w/w).

Water soluble polymers can serve to enhance the viscosity of a suspension and/or to stabilize nanoparticulate genistein against particle agglomeration or potential deleterious effects from other formulation components, for example. Water soluble polymers are pharmaceutically acceptable polymers that can be dissolved or dispersed in water. Suitable water soluble polymers include, without limitation, vegetable gums (e.g., alginates, pectin, guar gum, and xanthan gum), modified starches, polyvinylpyrrolidone (PVP), hypromellose (HPMC), methylcellulose, and other cellulose derivatives (e.g., sodium carboxymethylcellulose, hydroxypropylcellulose, and the like). In some embodiments, the genistein compositions described herein can include a poloxamer (e.g., Poloxamer 188) as a water soluble polymer. Poloxamer 188 is both a polymer and surfactant. The total water soluble polymer content in a genistein composition for use in the methods provided herein can range from about 0.5% to about 15% (w/w) [e.g., about 1% to about 10% (w/w), about 10% to about 15% (w/w), about 12% to about 15% (w/w), about 1% to about 8% (w/w), and about 1% to about 5% (w/w)].

Carriers suitable for use in the genistein formulations described herein also include pharmaceutically acceptable aqueous carriers such as, sterile water, physiologically buffered saline, Hank's solution, and Ringer's solution. The formulations also can contain one or more buffers [e.g., one or more citrate buffers, phosphate buffers, tris(hydroxymethyl)aminomethane (TRIS) buffers, and/or borate buffers], to achieve a desired pH and osmolality. Injectable pharmaceutical formulations typically have a pH in the range of about 2 to about 12. In some embodiments, the genistein formulations used in the methods provided herein can have a pH that falls in a range that more closely approximates physiologic pH (e.g., about 4 to about 8, or about 5 to about 7).

In some cases, the genistein compositions useful in the methods provided herein also can include one or more diluents. Suitable diluents include those selected from, without limitation, pharmaceutically acceptable buffers, solvents, and surfactants.

Moreover, in some embodiments, a genistein composition can include PVP (e.g., 5% PVP-K17) and polysorbate 80 (e.g., 0.2% polysorbate 80), as well as phosphate buffered saline (PBS, e.g., 50 nM PBS). In some cases, an oral formulation of a genistein composition can contain PVP (e.g., PVP-K25), polysorbate 80 (TWEEN® 80), and one or more preservatives (e.g., methyl paraben and/or propyl paraben). In addition, a composition can include a diluent such as a sodium chloride solution. In some cases, the particle size distribution of a nanoparticulate genistein composition can be $d(0.5) \leq 0.5$ microns (e.g., $d(0.5) \leq 0.4$ microns, $d(0.5) \leq 0.3$ microns, or $d(0.5) \leq 0.2$ microns). See, e.g., U.S. Pat. No. 8,551,530. It is to be noted that while such genistein formulations are characterized as suspensions, depending on the carriers, excipients, and diluents included in the suspension medium, a measurable amount of genistein also may be dissolved in the suspension medium.

A composition can contain genistein (e.g., nanoparticulate genistein or genistein that is not in nanoparticle form) at a concentration between about 100 mg/mL and about 500 mg/mL (e.g., about 100 mg/mL to about 400 mg/mL, about 150 mg/mL to about 350 mg/mL, about 200 mg/mL to about 400 mg/mL, about 250 mg/mL to about 350 mg/mL, about 250 mg/mL to about 500 mg/mL, about 275 mg/mL to about 325 mg/mL, about 300 mg/mL to about 450 mg/mL, or about 350 mg/mL to about 500 mg/mL). For example, a suspension of nanoparticulate genistein can incorporate genistein in an amount ranging from about 100 mg/mL to about 500 mg/mL (e.g., ranges from about 100 mg/mL to about 400 mg/mL, about 150 mg/mL to about 350 mg/mL, about 200 mg/mL to about 400 mg/mL, about 250 mg/mL to about 350 mg/mL, about 275 mg/mL to about 325 mg/mL, about 300 mg/mL to about 450 mg/mL, or about 350 mg/mL to about 500 mg/mL, or amounts of about 100 mg/mL, about 150 mg/mL, about 200 mg/mL, about 250 mg/mL, about 275 mg/mL, about 300 mg/mL, about 325 mg/mL, about 350 mg/mL, about 375 mg/mL, about 400 mg/mL, about 450 mg/mL, or about 500 mg/mL).

The relative amount of genistein included in a composition can be varied to yield a formulation having a desired total content of genistein. For example, a composition (e.g., a suspension formulation as described herein can include up to about 50% (w/w) genistein [e.g., about 50% (w/w), about 45% (w/w), about 40% (w/w), about 35% (w/w), about 30% (w/w), about 25% (w/w), about 20% (w/w), about 15% (w/w), about 10% (w/w), about 40% to about 50% (w/w), about 35% to about 45%, about 30% to about 40% (w/w), about 25% to about 35% (w/w), about 20% to about 30% (w/w), about 20% to about 35% (w/w), about 15% to about 35%, about 10% to about 30%, or about 10% to about 25%]. In some embodiments, nanoparticle genistein suspensions can provide increased bioavailability of genistein as compared to the bioavailability of genistein provided by solution formulations (e.g., solutions containing a pharmaceutically acceptable PEG solvent or containing larger sized genistein material). As described in U.S. Pat. No. 8,551,530, for example, the combination of high genistein loading and significantly increased bioavailability can provide advantages, such as facilitating administration of therapeutically effective amounts of genistein using much lower amounts of formulated drug substance, for example.

Genistein compositions can be formulated for administration by any suitable method, depending upon whether local or systemic treatment is desired and upon the area to be treated. For example, a genistein composition can be formulated for oral administration, parenteral administration (e.g., by subcutaneous, intrathecal, intraventricular, intramuscular, or intraperitoneal injection, or by intravenous drip), pulmonary administration (e.g., by inhalation or insufflation of powders or aerosols or a nebulized mist), or by a combination of routes such as oral and parenteral administration. Administration can be rapid (e.g., by injection) or can occur over a period of time (e.g., by slow infusion or administration of slow release formulations, such as from subcutaneous drug depots, slow short term intravenous injections, or slow release oral formulations).

Compositions and formulations for parenteral administration include, for example, sterile solutions (e.g., sterile aqueous solutions or suspensions) that also can contain buffers, diluents, and/or other suitable additives (e.g., penetration enhancers, carrier compounds and other pharmaceutically acceptable carriers). Compositions formulated for parenteral delivery can be manufactured according to standard methods to provide sterile compositions deliverable via, for example, intravenous injection or infusion, intravascular injection, subcutaneous injection, or intramuscular injection. A genistein formulation (e.g., a suspension of nanoparticulate genistein) can be prepared to have a viscosity suitable for the desired route of parenteral administration, and can be manufactured and packaged in any manner suited to the desired application, including, without limitation, as a formulation deliverable via intravenous injection or infusion, intravascular injection, subcutaneous injection, or intramuscular injection. In some embodiments, a formulation as described herein can be contained in one or more pre-filled syringes or auto-injectors prepared for administration of a given dose or range of doses of genistein.

Genistein compositions also can be formulated for oral administration. Compositions and formulations for oral administration include, for example, powders or granules, suspensions or solutions in water or non-aqueous media (e.g., suspensions of genistein nanoparticles in edible oil), capsules, gel caps, sachets, and tablets. In some embodiments, a genistein composition can be prepared as a liquid suspension that can be metered to deliver a desired dose, or can be incorporated into capsules (e.g., gelatin or soft capsules) suitable for delivery of liquid formulations. Alternatively, formulations for oral administration can be loaded into prefilled sachets or premetered dosing cups. In some embodiments, such genistein formulations also can include one or more pharmaceutically acceptable sweetening agents, preservatives, dyestuffs, flavorings, or any combination thereof. In some cases, genistein can be spray dried into a powder that subsequently can be hydrated to reconstitute a suspension.

Genistein compositions useful in the methods described herein can further include any pharmaceutically acceptable genistein salts, esters, or salts of such esters, or any other genistein compound which, upon administration to an animal such as a human, is capable of providing (directly or indirectly) biologically active genistein or an active metabolite or residue thereof. Accordingly, pharmaceutically acceptable salts of genistein, prodrugs and pharmaceutically acceptable salts of such prodrugs, and other bioequivalents can be used in the genistein compositions described herein. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of genistein (e.g., salts that retain the desired biological activity of genistein without imparting undesired toxicological effects). Examples of pharmaceutically acceptable salts include, for example, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., glucuronic acid, acetic acid, citric acid, oxalic acid, palmitic acid, or fumaric acid). Depending on the route of administration, for example, genistein may be sulfated or in glucuronic acid form.

Compositions also can include other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the genistein within the composition. The formulations can be sterilized if desired.

This document provides methods for using genistein compositions such as those described above. For example, the methods disclosed herein can include contacting a tumor cell, either in vitro or in vivo, with a genistein composition, such that the sensitivity of the tumor cell to radiation (e.g., higher LET proton radiation) is increased relative to a corresponding tumor cell that was not treated with the genistein composition.

In some embodiments, therefore, this document provides methods for sensitizing tumor cells to proton radiation (e.g., high LET proton radiation), where the methods include contacting the tumor cells with a composition that contains a pharmaceutically acceptable carrier and genistein (e.g., nanoparticulate genistein, where the composition contains nanoparticulate genistein at a concentration between about 250 mg/mL and about 500 mg/mL). Various types of tumors/tumor cells can be sensitized to radiation using the methods described herein. These include cells from solid tumors such as, without limitation, lung cancer (e.g., NSCLC) cells, prostate cancer cells, head and neck cancer cells, pancreatic cancer cells, colon/colorectal cancer cells, bladder cancer cells, thyroid cancer cells, breast cancer cells, liver cancer cells, ovarian cancer cells, endometrial cancer cells, cervical cancer cells, kidney cancer cells, brain cancer cells, and melanoma cells, as well as non-solid tumor cells such as non-Hodgkin lymphoma cells.

Tumor cells can be treated with a genistein composition prior to their irradiation with, e.g., high LET proton radiation. For example, tumor cells can be contacted with a genistein composition about 7 days to about 1 hour before radiation exposure. In some embodiments, the cells can be contacted with a genistein-containing composition about 6 to 7 days, about 5 to 6 days, about 4 to 5 days, about 3 to 4 days, about 60 to 72 hours, about 48 to 60 hours, about 36 to 48 hours, about 24 to 36 hours, about 18 to 24 hours, about 12 to 18 hours, about 10 to 12 hours, about 8 to 10 hours, about 6 to 8 hours, about 4 to 6 hours, about 2 to 4 hours, or about 1 to 2 hours before irradiation. In some cases, tumor cells can be contacted with a genistein composition about 20 to 28 hours (e.g., about 22 to 26 hours, or about 24 hours) before exposure to proton radiation.

This document also provides methods for treating a mammal (e.g., a human, or a non-human mammal such as, without limitation, a non-human primate, dog, cat, rat, rabbit, pig, sheep, mouse, cow, or horse) identified as having a solid tumor, where the mammal will undergo proton radiotherapy treatment, such as treatment with high LET proton radiation. The methods can include administering to the mammal a composition that contains a pharmaceutically acceptable carrier and genistein (e.g., nanoparticulate genistein as described herein). Again, a number of different tumor types can be treated using the methods provided herein, including lung tumors (e.g., NSCLC tumors), prostate tumors, head and neck tumors, pancreatic tumors, colon/colorectal tumors, bladder tumors, thyroid tumors, breast tumors, liver tumors, ovarian tumors, endometrial tumors, cervical tumors, kidney tumors, brain tumors, and melanomas, as well as non-Hodgkin lymphoma. In some embodiments, the tumor can include cells having a particular genetic signature or mutation (e.g., a KRAS or p53 signature or mutation; see, e.g., Loboda et al., *BMC Medical Genomics* 2010, 3:26; and Saleemuddin et al., *Gynecol Oncol.* 2008, 111(2):226-232) or the tumor can include cells expressing ERβ. Moreover, the mammal to be treated can be identified as having an alteration in one or more particular genes. For example, the mammal may be identified as having a rearrangement of the ALK gene, the RET gene, or the ROS1 gene, a mutation in the AKT1 gene, the BRAF gene, the DDR2 gene, the EGFR gene, the HER2 gene, the KRAS gene, the MEK1 gene, the NRAS gene, the PIK3CA gene, or the PTEN gene, and/or an amplification of the FGFR1 gene or the MET gene. Further, a mutation in the androgen receptor (AR) gene or the HOXB13 gene may be causative of a patient's cancer and differentiate genistein effectiveness. The development of cancer also may be linked to certain viral infections (e.g., human papillomavirus (HPV)). Viral-driven cancer may differentiate a tumor's response to radiation and/or genistein. In addition, inactivating mutations in DNA repair genes, such as ATM, ATR, BRCA1, BRCA2, PALB2, or MSH1, may affect how genistein modulates a patient's tumor-response to radiation. Methods for determining whether a mammal includes a particular genetic signature, marker, or mutation are typically well understood, and are described elsewhere.

The genistein-containing composition can be administered to the mammal beginning about an hour to about a week (e.g., six to seven days, five to six days, four to five days, three to four days, two to three days, one to two days, 12 to 24 hours, six to 18 hours, six to 12 hours, three to six hours, one to three hours, about seven, six, five, four, three, two, or one day, or about 18, 12, six, three, or one hour) before the onset of radiotherapy. Moreover, administration of the genistein-containing composition can be continued throughout the course of radiotherapy, and in some cases, after completion of the radiotherapy (e.g., for about one to seven days, one to two weeks, two to four weeks, four to six weeks, six to eight weeks, eight to ten weeks, or ten to twelve weeks). When administered, the genistein-containing composition can be given to the mammal at least once a day (e.g., once, twice, three times, or more than three times a day) before, during, and/or after the course of the radiotherapy treatment. In some cases, the administering can be such that the mammal receives a dose of about 100 mg/day to about 10,000 mg/day (e.g., about 250 to 500 mg/day, about 500 to 1,000 mg/day, about 1,000 to about 5,000 mg/day, or about 5,000 to about 10,000 mg/day).

The methods provided herein can include administering an effective dose of genistein to a mammal, where an "effective dose" provides a radio-sensitizing effect to cells of a particular type (e.g., tumor cells), enhancing a reduction in tumor size and/or number of tumor cells when combined with high LET proton radiation. The sensitization of a tumor to radiation therapy by genistein administration can mean that less radiation is needed for effective treatment than if genistein had not been administered. Thus, by use of the methods provided herein, a tumor can be effectively treated with a dose of radiotherapy that is at least about 5% (e.g., about 5%, about 10%, about 20%, about 30%, about 50%, or at least 75%) less than the dose of radiotherapy that would have to be administered to a corresponding tumor in a mammal not treated with the genistein-containing composition. The sensitization of a tumor to radiation therapy by genistein administration also can mean that the same dose of radiation has a greater therapeutic effect than it would have if genistein was not administered. Thus, by use of the methods provided herein, a dose of radiotherapy can have a therapeutic effect (e.g., on the size of a tumor or the number of cancer cells) that is at least about 5% (e.g., about 5%, about 10%, about 20%, about 30%, about 50%, or at least 75%) greater than the same dose's effect on a corresponding tumor in a mammal not treated with the genistein-containing composition.

The administering can be accomplished via any suitable route. In some embodiments, for example, a genistein composition containing a solution of genistein or a suspension of genistein nanoparticles can be administered orally (e.g., as a suspension) or parenterally (e.g., by injection, such as subcutaneous, intravenous, or intramuscular injection).

In some embodiments, the methods provided herein can include monitoring a mammal treated with genistein and proton radiation to determine whether the number of cancer cells or the size of a tumor is diminished after treatment. Any appropriate method can be used to determine whether or not the number of cancer cells or the size of a tumor present within a mammal is reduced. For example, imaging techniques can be used to assess the number of cancer cells and/or the size of a tumor present within a mammal.

The invention will be further described in the following example, which does not limit the scope of the invention described in the claims.

EXAMPLE

Effect of Genistein Pre-Treatment on Cell Survival After Exposure to Various Forms of Radiation Studies were conducted to determine whether a nanoparticulate genistein formulation affects cellular radiosensitivity to protons with increasing LET. Normal and cancer cell lines were exposed to low, intermediate, or high LET proton radiation. These experiments used the H1299 and H460 NSCLC cell lines, which are relevant to lung cancer research during medical radiation exposure as well as nonmedical or accidental radiation exposure. These cell lines were derived from human cancer patients and have well-known radiobiologic properties, with H1299 being relatively less radiosensitive. Both lines harbor Ras pathway activating mutations (H460, KRAS; H1299, NRAS). MRC5 human lung fibroblasts also were used as representative normal cells. Each cell line was obtained from the American Type Culture Collection (ATCC) and tested for mycoplasma regularly. Clonogenic cell survival studies were performed as described elsewhere (Cengel et al., *Neoplasia* 9(4):341-348, 2007). Briefly, cells were plated 24 hours prior to radiation at about 50% confluence. After allowing attachment, culture media was supplemented with 5 µM nanoparticulate genistein or the equivalent volume of inactive vehicle. Cells were radµated using either 250 KVp x-rays or protons with lower vs. higher LET. To vary the proton LET, cell dishes were placed at a depth of 2 cm (D2, low LET) or 10 cm (D10, high LET) in a R10.5M5 double scattered proton beam—a double scattered proton beam with a maximum range of 10.5 cm and a modulated depth of 5 cm, meaning that the Spread-out Bragg peak (SOBP) began roughly at a depth of 5.5 cm. In this configuration, the D2 and D10 positions corresponded to the entrance and terminal portions of the SOBP, respectively. After exposure to radiation, cells were trypsinized into a single cell suspension and re-plated at various densities without nanoparticulate genistein. About two weeks later (typically 13 to 16 days, depending on colony size), plates were rinsed and stained using crystal violet/ethanol, and colonies were enumerated using an Oxford Optronix automated colony counter with a minimum threshold size of 50 cells to define a colony. All experiments were performed a minimum of three times with at least six replicate dishes per condition. Data were then fit using a linear-quadratic (LQ) function of the form:

$$\text{Surviving Fraction (Dose)} = e^{-(\alpha D + \beta D^2)}$$

Relative radiosensitivity was numerically compared using a standard variable, $D_0$ (the dose of radiation needed to reduce the surviving fraction by a factor of 1/e), which was determined from the positive solution to the quadratic equation of the form:

$$\beta D^2 + \alpha D - 1 = 0,$$

where $\alpha$ and $\beta$ are determined from the LQ survival curve fit as above. The Dose Modifying Factor (DMF) was determined by the quotient:

$$\text{Dose Modifying Factor } (DMF) = \frac{D_0(\text{Vehicle treated cells})}{D_0(\text{Genistein treated cells})}$$

As a standard criterion, radiosensitization was defined as DMF>1.1.

Figure 2A:
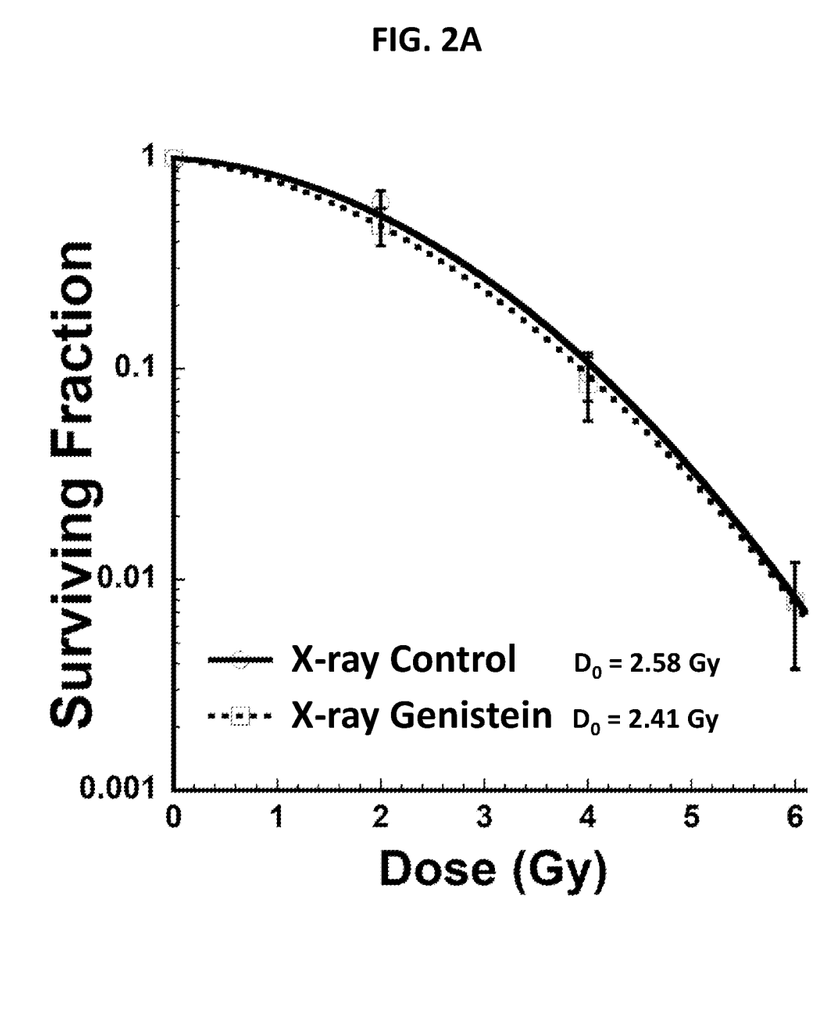
FIGS. 2A and 2B are graphs plotting the survival of H460 human non-small cell lung cancer (NSCLC) cells treated with or without a nanoparticulate genistein composition 24 hours before being exposed to the indicated doses of X-Ray (FIG. 2A) or high LET proton (FIG. 2B) radiation.
Figure 2B:
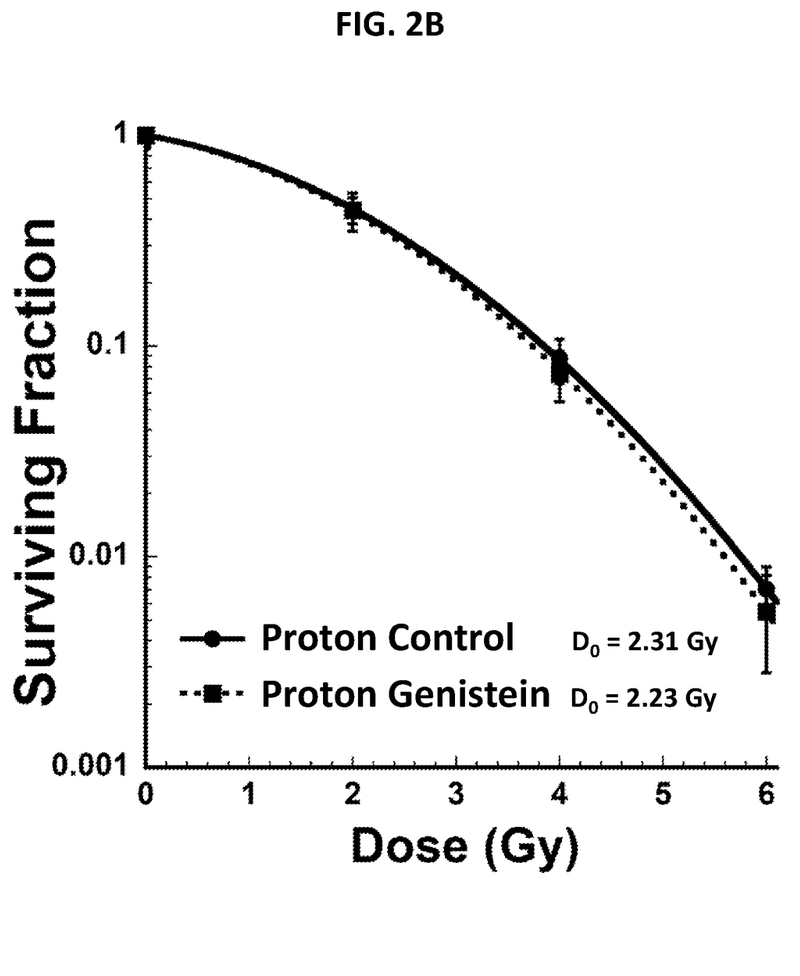
Figure 3A:
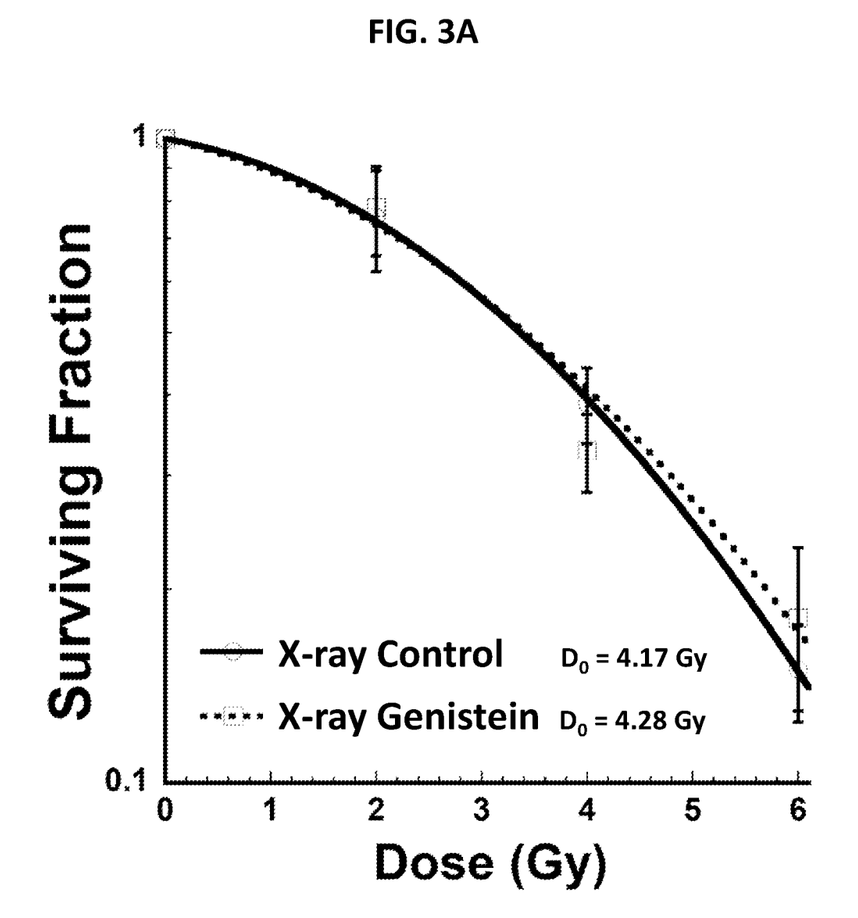
FIGS. 3A and 3B are graphs plotting the survival of H1299 human NSCLC cells treated with or without a nanoparticulate genistein composition 24 hours before being exposed to the indicated doses of X-Ray (FIG. 3A) or high LET proton (FIG. 3B) radiation.
Figure 3B:
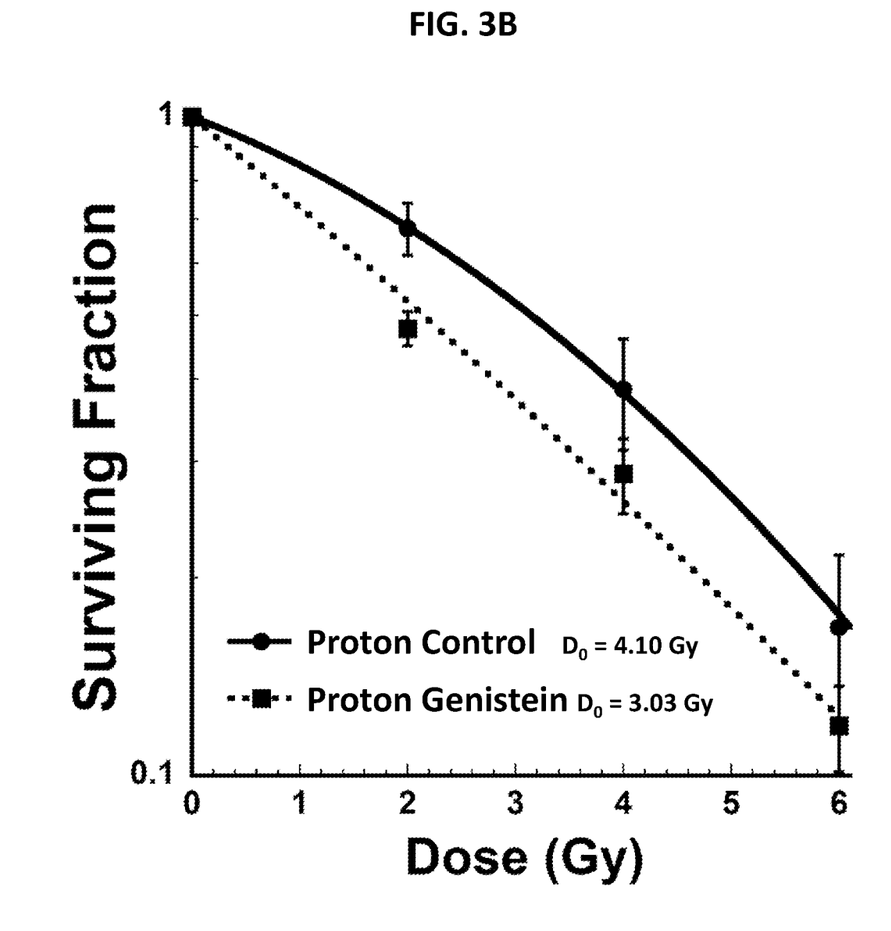
Figure 4A:
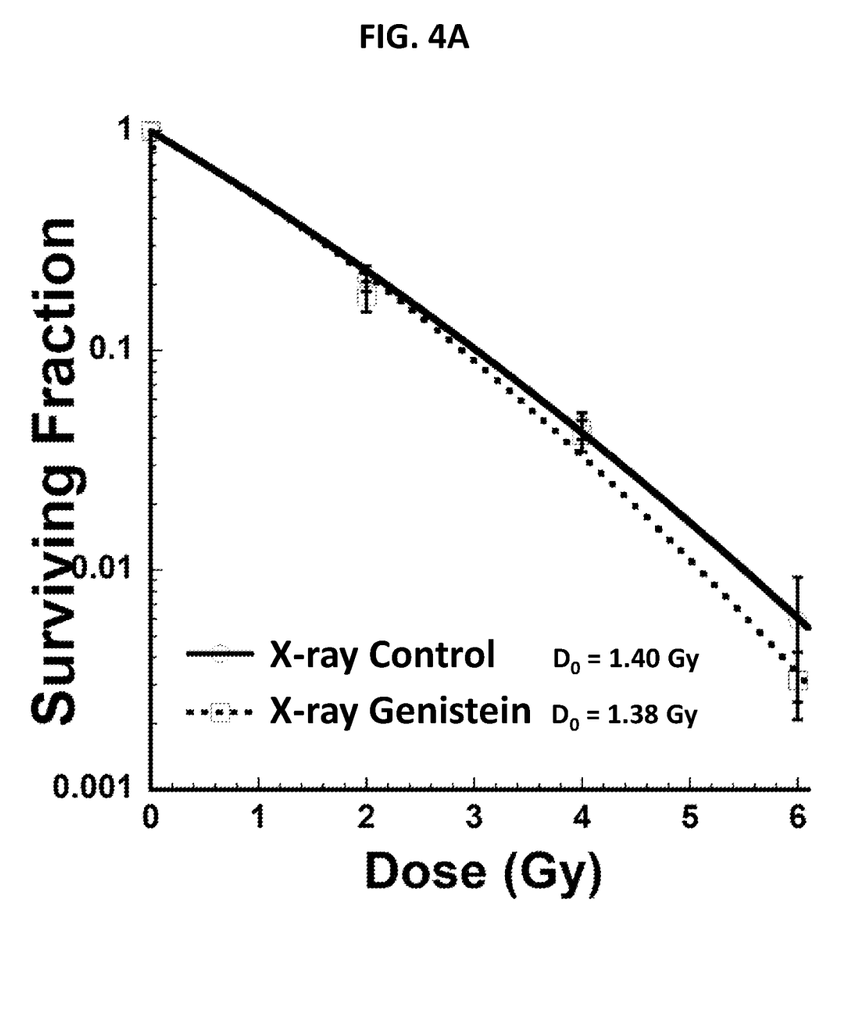
FIGS. 4A and 4B are graphs plotting the survival of MRC5 normal human lung fibroblasts treated with or without a nanoparticulate genistein composition 24 hours before being exposed to the indicated doses of X-Ray (FIG. 4A) or high LET proton (FIG. 4B) radiation.
Figure 4B:
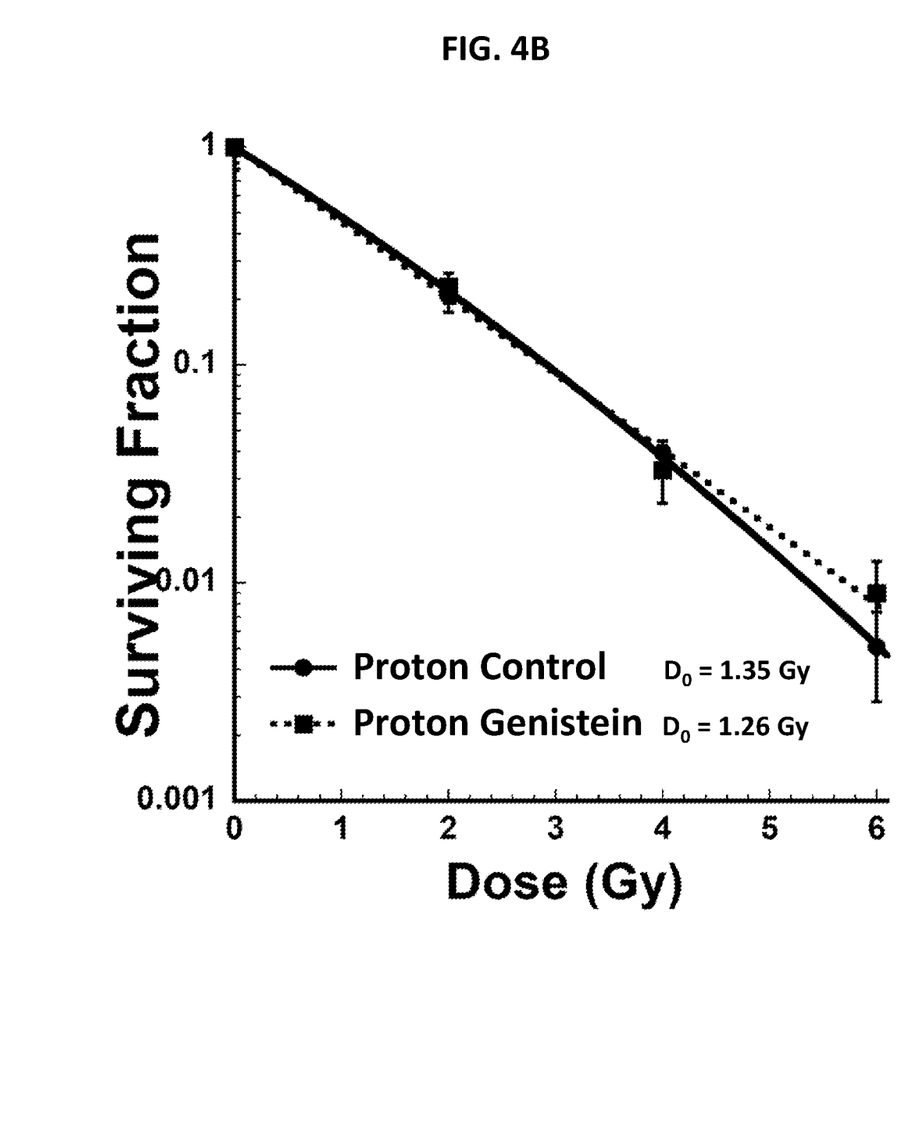

The results of these experiments demonstrated that the nanoparticulate genistein composition had LET-dependent and cell line-specific effects on radiosensitivity of lung cancer cells. The genistein composition did not change the radiosensitivity of H460 cells, regardless of LET or radiation type (FIGS. 2A and 2B), with a DMF of 1.07 for X-Rays and 1.04 for higher LET protons. These cells showed modest, LET-dependent radiosensitization with a DMF of 1.12 for X-Rays vs higher LET protons in the absence of genistein. In contrast, the nanoparticulate genistein composition exhibited clear LET-dependent radiosensitization for H1299 cells, with a DMF of 0.97 for X-Rays and, interestingly, 1.35 for higher LET protons (FIGS. 3A and 3B). The LET (rather than radiation-type) specificity of this effect was confirmed in experiments using lower LET protons in which the genistein composition failed to radiosensitize H1299 cells (DMF=1.09). Finally, nanoparticulate genistein had no significant effect on clonogenic survival of normal human fibroblast cells, with a DMF of 1.01 and 1.07 for X-Rays and higher LET protons, respectively (FIGS. 4A and 4B). These results are summarized in TABLE 1.

TABLE 1

Cell survival after radiation exposure with and without genistein pre-treatment

| | X-Rays | | | High LET Protons | | |
|---|---|---|---|---|---|---|
| Cell Line | Vehicle ($D_0$) | Genistein ($D_0$) | DMF | Vehicle ($D_0$) | Genistein ($D_0$) | DMF |
| H460 | 2.58 | 2.41 | 1.07 | 2.31 | 2.23 | 1.04 |
| H1299 | 4.17 | 4.28 | 0.97 | 4.10 | 3.03 | 1.35 |
| MRC5 | 1.40 | 1.38 | 1.01 | 1.35 | 1.26 | 1.07 |

In cancer radiotherapy, patients typically receive 60 Gy of radiation in 2 Gy daily doses. A DMF of 1.35 means that patients who receive the nanoparticulate genistein composition disclosed herein would get a tumor equivalent of 60 Gy×1.35=81 Gy effective dose, such that the tumor would be hit much harder by the radiation.

This information also can be used to determine the dose of high LET proton radiation necessary to effectively treat the tumor. In particular, a DMF of 1.35 means that rather than 60 Gy, a patient treated with a nanoparticulate genistein composition could be treated with 60 Gy/1.35=44 Gy of high LET proton radiation to achieve the same therapeutic effect as 60 Gy in a patient who did not receive the genistein composition.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for sensitizing tumor cells to high linear energy transfer (LET) proton radiation, the method consisting essentially of:
   contacting the tumor cells with a composition consisting essentially of one or more pharmaceutically acceptable carriers and nanoparticulate genistein, wherein the tumor cells are contacted with the nanoparticulate genistein at a concentration of 5 uM (micromolar), and
   contacting the tumor cells with the high LET proton radiation, wherein the genistein is effective to sensitize the tumor cells to the proton radiation, in a manner that the tumor cells are reduced in number and therapeutically effectively treated with a dose of the high LET proton radiotherapy that is at least 10% less than a dose of high LET proton radiotherapy that would need to be administered to corresponding number of tumor cells not treated with the genistein composition.

2. The method of claim 1, wherein the tumor cells are lung cancer cells, prostate cancer cells, head and neck cancer cells, pancreatic cancer cells, colon/colorectal cancer cells, bladder cancer cells, thyroid cancer cells, breast cancer cells, liver cancer cells, ovarian cancer cells, endometrial cancer cells, cervical cancer cells, kidney cancer cells, brain cancer cells, or melanoma cells.

3. The method of claim 1, wherein the tumor cells are non-small cell lung cancer (NSCLC) cells.

4. The method of claim 1, wherein the step of contacting the tumor cells with the composition is carried out 1 to 4 hours prior to the step of contacting the tumor cells with the high LET proton radiation.

5. The method of claim 1, wherein the genistein is present in the composition at a concentration of 100 mg/mL to 500 mg/mL.

6. A method for treating a mammal identified as having a solid tumor and slated to undergo treatment with high linear energy transfer (LET) proton radiotherapy, the method consisting essentially of:
   administering to the mammal a composition consisting essentially of one or more pharmaceutically acceptable carriers and nanoparticulate genistein, wherein the composition is administered in a manner that cells of the solid tumor are contacted with the nanoparticulate genistein at a concentration of 5 µM, and exposing the solid tumor in the mammal to high LET proton radiation, wherein the genistein is effective to sensitize cells of the solid tumor to the proton radiation, in a manner that the tumor is therapeutically effectively treated and the cells in the tumor are reduced in number with a dose of the high LET proton radiotherapy that is at least 10% less than a dose of high LET proton radiotherapy that would need to be administered to a corresponding tumor in a mammal not treated with the composition.

7. The method of claim 6, wherein the step of administering the composition to the mammal is carried out 1 to 3 hours before the onset of administering the high LET proton radiation.

8. The method of claim 6, wherein the step of administering the composition to the mammal is carried out at least once a day during the course of administering the high LET proton radiation.

9. The method of claim 6, wherein the tumor is a lung tumor, a prostate tumor, a head and neck tumor, a pancreatic tumor, a colon/colorectal tumor, a bladder tumor, a thyroid tumor, a breast tumor, a liver tumor, an ovarian tumor, an endometrial tumor, a cervical tumor, a kidney tumor, a brain tumor, or a melanoma.

10. The method of claim 6, wherein the tumor is a NSCLC tumor.

11. The method of claim 6, wherein the mammal is a human.

12. The method of claim 6, wherein the administering is at a dose of 1000 mg/day to 5000 mg/day.

13. The method of claim 6, wherein the tumor comprises cells that express estrogen receptor β (ERβ).

14. The method of claim 6, wherein the one or more pharmaceutically acceptable carriers form a suspension medium, and wherein the one or more pharmaceutically acceptable carriers comprise a water soluble polymer comprising a polyvinylpyrrolidone.

15. The method of claim 6, wherein the genistein is present in the composition at an amount ranging up to 50% (w/w).

16. The method of claim 6, wherein the composition has a genistein concentration of 325 mg/mL.

17. The method of claim 6, wherein the administering is oral, intramuscular, subcutaneous, or intravenous.

18. The method of claim 6, wherein the genistein is present in the composition at a concentration of 100 mg/mL to 500 mg/mL.

* * * * *